(12) United States Patent
Snyder

(10) Patent No.: US 6,222,371 B1
(45) Date of Patent: Apr. 24, 2001

(54) HAND-HELD FLUID TESTER FOR PROCESS FLUIDS

(75) Inventor: Francis J. Snyder, Ontario, NY (US)

(73) Assignee: Pulsafeeder, Inc., Rochester, NY (US)

( * ) Notice: Subject to any disclaimer, the term of this patent is extended or adjusted under 35 U.S.C. 154(b) by 0 days.

(21) Appl. No.: 08/956,209

(22) Filed: Oct. 22, 1997

(51) Int. Cl.[7] .................................................. G01N 27/02
(52) U.S. Cl. ........................ 324/439; 324/438; 324/441; 204/194
(58) Field of Search ...................... 324/438, 439, 324/441, 444, 450, 722, 724; 204/193, 194, 400, 401, 402, 406, 407, 408, 409, 422, 452

(56) References Cited

U.S. PATENT DOCUMENTS

| | | | |
|---|---|---|---|
| 4,303,887 | * 12/1981 | Hill et al. .............................. | 324/441 |
| 4,994,397 | * 2/1991 | Pagel .................................... | 204/406 |
| 5,269,891 | * 12/1993 | Colin .................................... | 204/402 |
| 5,644,239 | * 7/1997 | Huang et al. ......................... | 324/439 |
| 5,747,666 | * 5/1998 | Willis ................................... | 324/438 |
| 5,821,399 | * 10/1998 | Zelin .................................... | 324/439 |

* cited by examiner

Primary Examiner—Diep Do
(74) Attorney, Agent, or Firm—Hill & Simpson

(57) ABSTRACT

A portable, hand-held fluid tester for testing and analyzing process fluids is provided with a volume controlled fluid reservoir. The test fluid reservoir is connected by a spillway to an overflow reservoir to provide more consistent and accurate fluid volumes for measurement. Improved mounting of electrodes in the test reservoir and connection to a testing printed circuit substrate provides for ease of assembly. A special temperature probe arrangement is also provided in a preferred embodiment.

16 Claims, 3 Drawing Sheets

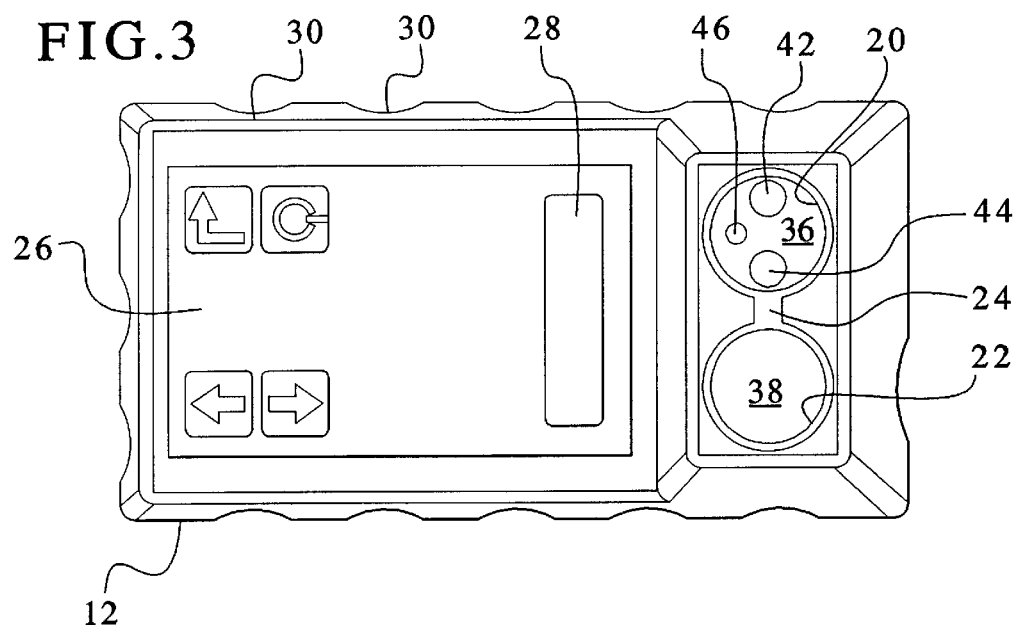
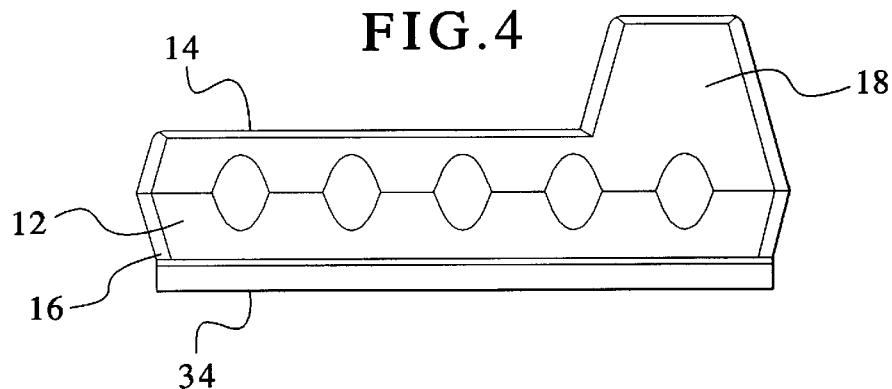
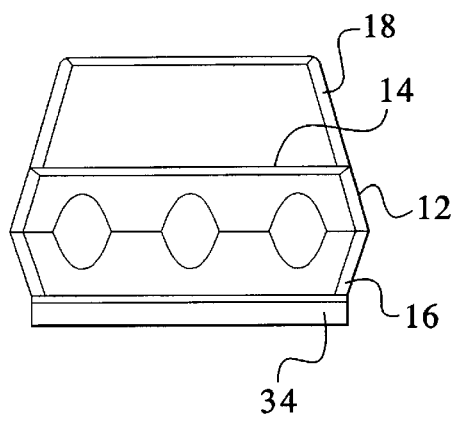
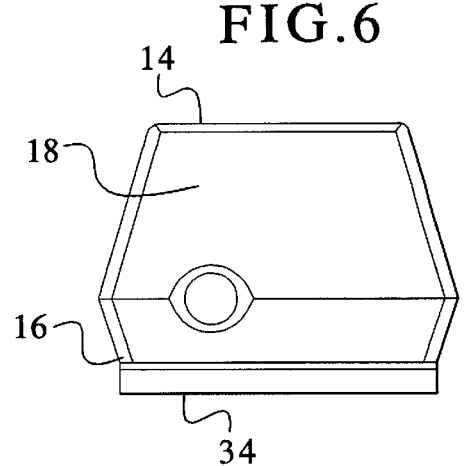

HAND-HELD FLUID TESTER FOR PROCESS FLUIDS

BACKGROUND OF THE INVENTION

The present invention generally relates to portable, hand-held fluid testers for measuring the properties of a test fluid in the field. More particularly, it relates to a new and improved portable, hand-held fluid tester having improved sealing and assembly, electrical connection and fluid volume control features.

Hand-held fluid testers are currently available for measuring electrical conductivity of a process fluid such as boiler fluids or coolant fluids. These fluid testers include a fluid reservoir which contains electrodes to measure the electrical conductivity of the fluid in the reservoir. The electrodes are connected to a circuit board via jumper wires. Some models also include a thermistor to provide temperature compensation for more accurate measurement. If employed, the thermistor is typically mounted in a hole adjacent the fluid reservoir with a thin wall separation which sometimes breaks into the reservoir. These thermistors are usually connected to the printed circuit board via jumper wires. In some models, the thermistor is potted into place with a potting compound to both assemble the thermistor to the fluid reservoir and to insure sealing of any thin wall imperfections. With these conventional hand-held fluid testers, testing is performed by filling the fluid reservoir to a marked volume. This is typically done by line of sight and therefore the volume of test fluid introduced to the fluid reservoir may not be the same for all tests and may vary depending on the person doing the testing.

These conventional hand-held fluid testers have a number of important shortcomings. For example, the assembly of the electrodes and the thermistor to the reservoir wall is cumbersome and frequently requires the use of additional potting compounds or adhesives which are difficult to handle. The electrical connections between these devices and a testing circuit on a printed circuit board are typically provided via jumper wire leads which also must be individually handled and connected which increases labor associated with the assembly. Moreover, these devices do not provide any inherent test fluid volume controls so that wide variations in test results of and a lack of any meaningful calibration leads to unreliable results.

SUMMARY OF THE INVENTION

To overcome these and other shortcomings of the prior art devices, the present nvention provides a new and improved portable, hand-held fluid tester. In an embodiment, the portable, hand-held fluid tester comprises a tester body configured to be held in the hand including an upper surface and an opposed bottom surface. A first recess extends inwardly from the upper surface to a first end wall and defines a fluid reservoir for receiving a test fluid to be tested. A second recess extends inwardly from the upper surface to a second end wall to define an overflow reservoir which is disposed adjacent to the fluid reservoir. An angled spillway surface extends between and interconnects an upper end of the fluid reservoir to an upper end of the overflow reservoir.

A third recess extends inwardly from the bottom surface to a third end wall to define a test circuit receiving recess. At least one test probe member extends from the third wall into the first end wall and fluid reservoir and is sealingly engaged in the tester body. A test circuit in the test circuit receiving recess is operably connected with said at least one probe member for measuring at least one parameter of the test fluid introduced in the test fluid reservoir and reporting a result for the at least one parameter measurement. The fluid tester additionally includes a cover member releasably secured to the tester body closing off an opening of the third recess.

A major advantage provided by the new and improved hand-held fluid tester of the present invention is that the fluid tester is designed to provide repeatable test results by providing constant volume of fluid being tested. This feature is provided, inter alia, by the addition of a spillway to the wall of the test reservoir. The angled spillway surface is configured to overflow excess test fluid introduced in the fluid reservoir from the fluid reservoir to the overflow reservoir, thereby defining a maximum fluid volume for the fluid reservoir. Once the fluid level reaches the spillway, excess fluid is automatically drained off to insure a constant volume for the test fluid from test to test and from user to user leading to more consistent and accurate testing results.

In an embodiment, the portable, hand-held tester is provided for measuring electrical conductivity of a process fluid and in accordance with this embodiment, the at least one test probe member comprises a pair of cylindrical metallic electrodes each having a front end and an opposed rear end. The electrodes are mounted in the tester housing so that they extend into the third end wall with the front end of each electrode flush mounted in the first end wall of the fluid reservoir. Each electrode includes an external o-ring groove and an o-ring disposed in the groove by means of which each electrode is sealingly mounted in the tester housing.

In a preferred embodiment, the rear end of each electrode includes a threaded recess and the test circuit comprises a printed circuit substrate mounted in the test circuit receiving cavity. A pair of threaded mounting screws extend through the printed circuit substrate and each is respectively threadingly engaged in a threaded recess of an electrode to thereby electrically and mechanically connect the electrode with the test circuit. In accordance with this embodiment, lead wires are not necessary and a direct leadless connection is made between the electrodes and the test circuit substrate. This feature provides a more reliable assembly and electrical connection of the probes to the circuit board. This advantage is accomplished by providing a direct circuit board mounting of the probes.

In an embodiment, the portable, hand-held fluid tester further comprises a temperature probe. The temperature probe comprises a hollow cylindrical metal housing having a closed front end and an opposed open rear end with an elongate cylindrical thermistor receiving recess defined therein. A thermally conductive grease may be disposed in the thermistor receiving recess adjacent the closed front end. A thermistor operably connected with the test circuit is disposed in the thermistor receiving recess adjacent the closed front end in contact with the thermally conductive grease. The temperature probe extends into the third end wall of the tester housing with its closed front end extending into the first end wall and fluid reservoir. The temperature probe is sealingly mounted in the tester housing.

In a preferred embodiment, the sealed mounting of the temperature probe in the tester housing is provided by an external o-ring groove on the cylindrical metal housing and an o-ring disposed in said groove which is compressingly, sealingly engaged with the tester housing.

In accordance with this aspect of the invention, major advantages are provided because the arrangement provides faster and more reliable temperature compensation with improved sealing and assembly. This feature is accomplished by placing the thermistor in a thermal well of metallic material, more suited for heat transfer than standard potting compounds. The thermal well is inserted and sealed as a separate item and is therefore easily replaced and assembled with respect to the circuit board and housing.

Other objects and advantages provided by the present invention will become apparent from the following detailed description taken in conjunction with the drawings in which:

BRIEF DESCRIPTION OF THE DRAWINGS

FIG. 3 is a top plan view of the new and improved portable, hand-held fluid tester shown in FIG. 1;

FIG. 4 is a side elevation view of the new and improved portable, hand-held fluid tester shown in FIG. 1;

FIG. 5 is an end elevation view of the left end of the new and improved portable, hand-held fluid tester shown in FIG. 1;

FIG. 6 is an end elevation view of the right end of the new and improved portable, hand-held fluid tester shown in FIG. 1.

DETAILED DESCRIPTION OF THE PREFERRED EMBODIMENTS

Figure 1:
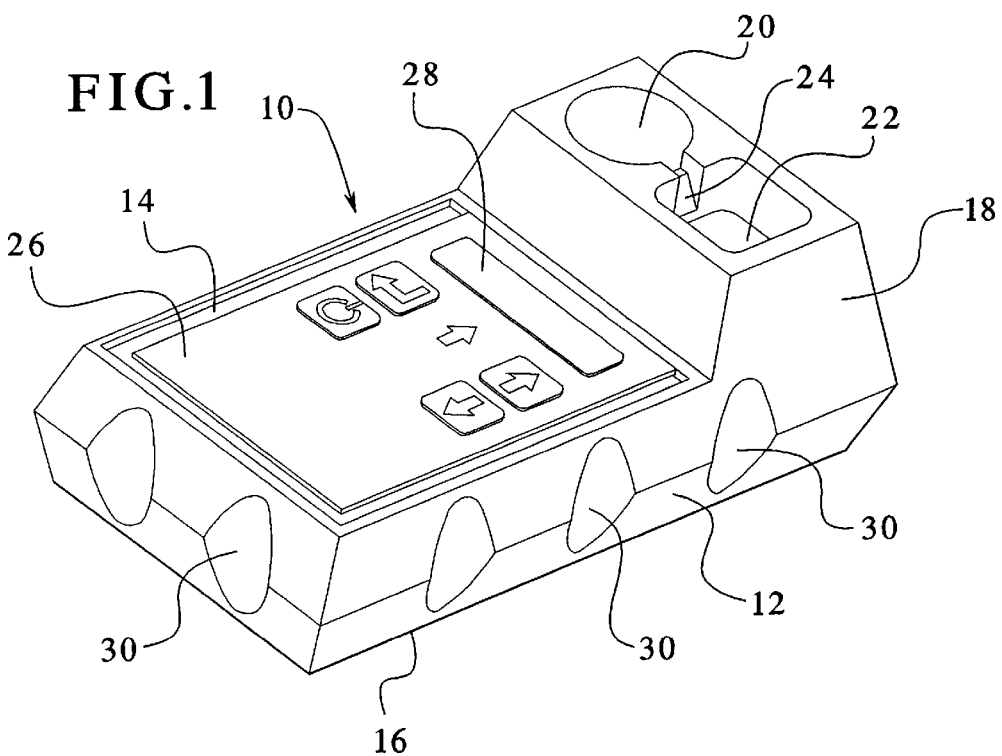
FIG. 1 is a perspective view of the new and improved portable, hand-held fluid tester in accordance with a preferred embodiment of the invention.

Referring now to FIG. 1, a new and improved portable, hand-held fluid tester in accordance with a preferred embodiment of this invention, generally referred to by reference numeral 10, as shown. Fluid tester 10 is of a type for readily testing process fluids for a relevant parameter. For example, the hand-held tester may be configured and used to test process fluids such as boiler fluids or coolant fluids by testing their electrical conductivity to determine concentration of ions present. The fluid tester might also test a sample fluid for pH. In addition, swimming pool fluid or the like could be tested for oxidation reduction potential (ORP) with a hand-held fluid tester such as fluid tester 10 provided the appropriate probes and circuitry were incorporated therein. For purposes of illustration, fluid tester 10 is adapted to test the electrical conductivity of a test fluid.

In greater detail, and as shown in FIG. 1, portable, hand-held fluid tester 10 comprises a tester body 12 having a generally rectangular configuration including an upper surface 14 and an opposed bottom surface 16. Tester body 12 includes an enlarged front end 18 including a first recess 20 defining a fluid reservoir and a second recess 22 defining an overflow reservoir. An angled spillway surface 24 is provided adjacent an upper end of fluid reservoir 20 and an upper end of overflow reservoir 22.

In the preferred embodiment depicted in FIG. 1, a keypad data input entry device 26 is provided in upper surface 14. The keypad 26 preferably includes a display window 28 for displaying input commands under software controlled programming and for displaying the result of testing.

In the preferred embodiment depicted in FIG. 1, oval depressions 30 are provided in the upstanding sidewalls of the tester body 12 to provide comfortable finger grip locations for a more ergonomic hand-held design.

Tester body 12 preferably comprises a engineering thermoplastic material. Preferably, tester body 12 comprises a unitary or one-piece thermoplastic molding. The tester body may be molded from any suitable engineering thermoplastic molding resin which is non-reactive with respect to the test fluids being tested. Illustrative examples may include polyolefins, polyesters, polycarbonates to name but a few materials. In accordance with a preferred embodiment, the tester body preferably comprises a molded thermoplastic polyester resin.

As shown in FIGS. 2 and 4–7, hand-held fluid tester 10 additionally comprises a third recess 32 extending inwardly from the bottom surface of tester body 12 and defining a test circuit receiving recess. A cover member 34 is provided for releasable securement to tester body 12 to selectively close off an opening to test circuit receiving recess 32.

Figure 7:
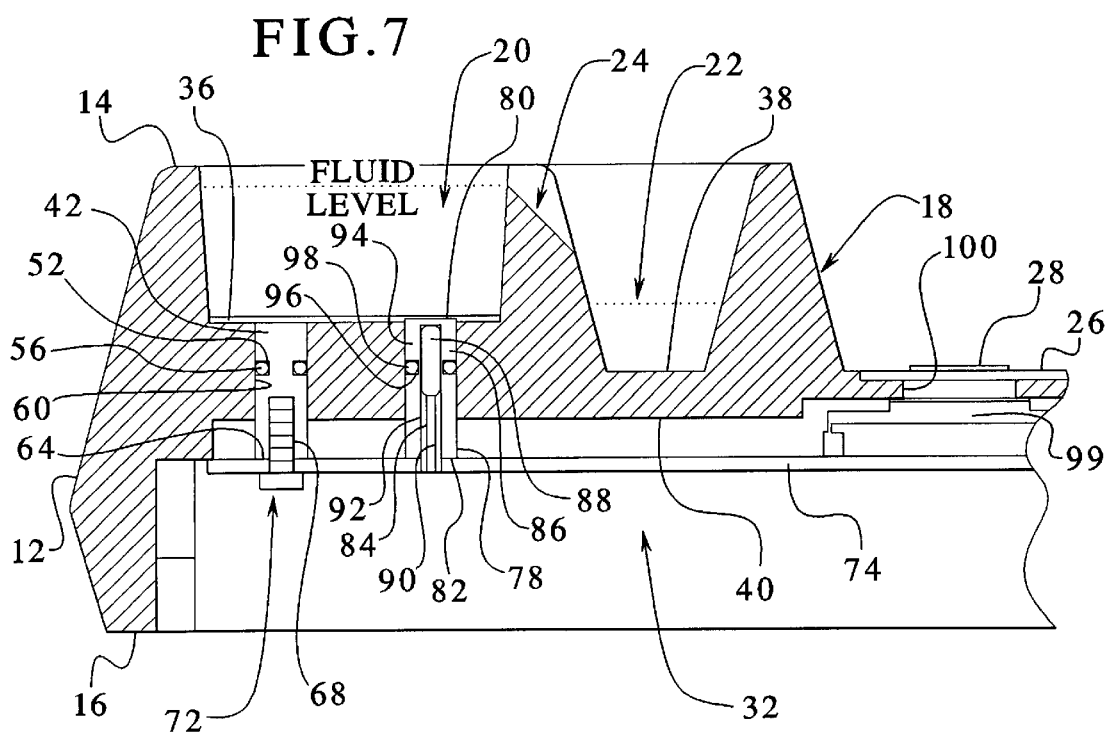
FIG. 7 is a fragmentary elevated cross sectional view of the new and improved portable, hand-held fluid tester shown in FIG. 1.

As shown in FIGS. 3 and 7, the fluid reservoir 20 extends inwardly from an opening in upper surface 14 to a first end wall 36 disposed within tester body 12. The overflow recess 22 extends inwardly from an opening adjacent upper surface 14 to a second end wall 32 disposed inwardly within tester body 12 at a shallower, the same or deeper level than first end wall 36. As shown in FIG. 7, the test circuit receiving recess 32 extends inwardly from an opening adjacent the bottom surface 16 to a third end wall 40.

Figure 2:
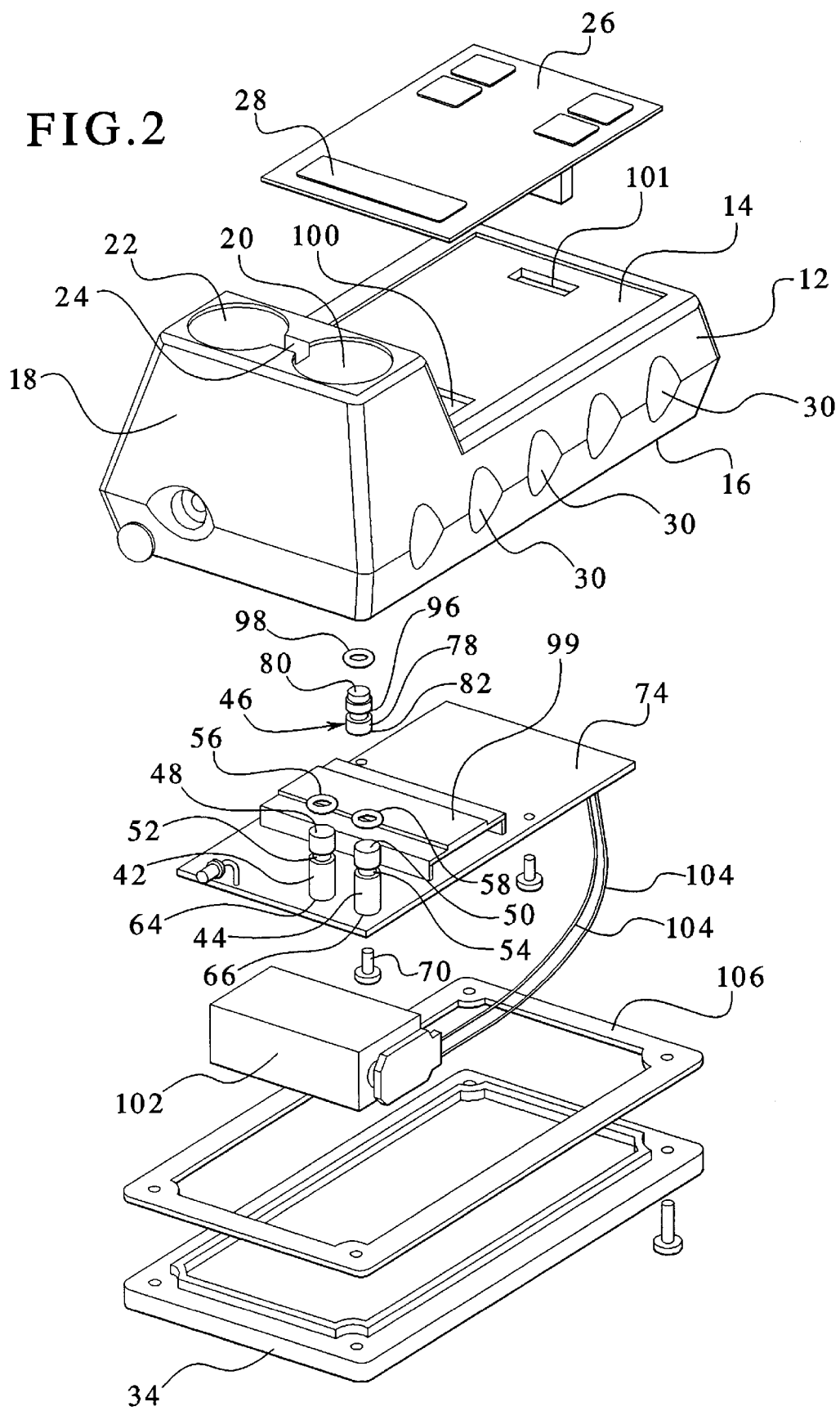
FIG. 2 is an exploded perspective view of the new and improved portable, handheld fluid tester shown in FIG. 1.

As shown in FIGS. 2, 3 and 7, a first electrode 42, a second electrode 44 and a temperature probe 46 are mounted within tester body 12 so that they extend into the third end wall 40 and extend toward first end wall 36 at which their front end surfaces are flush mounted and exposed to the fluid reservoir 20.

As is best shown in FIGS. 2 and 7, first electrode 42 and second electrode 44 comprise a pair of cylindrical metallic electrodes each having a front end 48 and 50 respectively flush mounted in the first end wall 36. First and second electrodes 42 and 44 are preferably each provided with an external o-ring groove 52 and 54 respectively adapted to receive o-rings 56 and 58 respectively for sealed, fluid type engagement and mounting in the cylindrical passageways 60 and 62 respectively extending in tester body 12 between the third end wall 40 and the first end wall 36. Moreover each electrode 42 and 44 includes a rear end 64 and 66 respectively each including a threaded recess 68 and 70 for receiving a mounting and connecting screw 72 which is mounted through a printed circuit substrate 74 comprising a part of a test circuit 76. In fully engaged and threaded positions, screws 72 are effective to electrically and mechanically connect electrodes 42 and 44 to conductive regions defined on printed circuit substrate 74.

In the preferred embodiment depicted in FIGS. 2, 3 and 7, hand-held fluid tester 10 additionally includes the temperature probe 46. Temperature probe 46 comprises a hollow cylindrical metal housing 78 having a closed front end 80 and an opposed open rear end 82. An elongate cylindrical thermistor receiving recess 84 is defined within hollow housing 78. Preferably a thermally conductive grease such as a silicone thermally conductive grease 86 is disposed in the thermistor receiving recess 84 adjacent the closed front end 80. Temperature probe 46 further comprises a thermistor 88 disposed in a thermistor receiving recess 84 adjacent the closed front end 80 in contact with the thermally conductive grease 86. Thermistor leads 90 and 92 extend from the temperature probe 46 for electrical connection to circuit elements provided on printed circuit substrate 74. Temperature probe 46 is mounted in tester body 12 extending into a cylindrical passage 94 extending from third end wall 40 to an opening in the first end wall 36. Temperature probe 46 is inserted into passage 94 so that its closed front end 80 is flush mounted with first end wall 36 in fluid reservoir 20. As shown in the preferred embodiment depicted in the drawings, hollow housing 78 includes an external o-ring groove 96 and o-ring 98 for forming sealed fluid-tight engagement within cylindrical passage 94 of tester body 12.

Test circuit 76 may be of the type well known to those skilled in this art for performing electrical conductivity testing and for directing a sequence of testing steps under the command of a microprocessor associated with the printed circuit substrate 74 in a manner well known to those skilled in this art. An LCD or LED display 99 may be mounted on the substrate 74 in a position to be seen through display window 28. A rectangular display cutout 100 may be provided in upper surface 14 as shown in FIG. 2. Similarly, a rectangular cutout 101 to permit passage of electrical leads from the keypad input device 26 through upper surface 14 for electrical attachment to printed circuit substrate 74 may also be provided. In accordance with the preferred embodiment depicted in the drawings, the LCD or LED display 99 may comprise one or several digital displays of a type well known to those skilled in the art. The testing circuitry for measuring electrical conductivity of the test fluid applies a voltage to the first electrode 42, the and second electrode 44 shares a common reference to the first and thus a current flows between the two electrodes and the circuitry and measures the current flowing therebetween through the test fluid to determine the electrical conductivity of the test fluid. This may give an indirect indication of ionic concentration of ion species within the test fluid. The circuitry may activate the temperature probe to obtain a temperature reading and thereafter correct the measurement result to account for variations in temperature in the manner known to those skilled in the art. Internal programming of the microprocessor can provide any necessary calibration sub-routines which may be required to improve the accuracy of the device in a manner generally known to those skilled in the art.

As shown in FIG. 2, the test circuit 76 and its associated printed circuit substrate 74 may be powered by means of a battery 102 connected to leads 104.

As indicated in FIG. 2, the entire portable, hand-held fluid tester 10 may be assembled by mounting the electrodes and thermistor to the printed circuit substrate. And thereafter press fitting these elements into their respective cylindrical passageways, 60, 62 and 94 and mounting the printed circuit substrate 74 within the test circuit receiving recess 32 by means of appropriate mounting screws, mounting apertures and molded in threaded screw receiving recesses provided in the tester body in accordance with mounting methods well known to those skilled in the art. As shown in FIG. 2, a sealing gasket 106 may also be provided which is sealingly compressed between cover member 34 and the opening to the test circuit receiving recess 32 to provide a sealed test circuit receiving enclosure.

Although the present invention has been described with reference to a preferred embodiment shown in the drawings, modifications or changes may be made therein by those skilled in this art. For example, instead of a keyed input system, a simple on/off switch might be provided to start and stop a testing subroutines. Instead of a visual display readout for the test circuit, another indicator of test results might be provided. For example, instead of a visual display, an audible signal indicative of a pass or fail condition might be activated by the test circuit in response to the measured parameter being tested for. Although the hand-held fluid tester described in connection with the preferred embodiment tested electrical conductivity through electrodes 42 and 44, different probe arrangements and different circuitry or circuit options might be provided through software programming and circuitry or the like to test a test fluid for different parameters including pH, oxidation reduction potential (ORP), turbidity or the like. These additional testing probes may be attached as supplemental probe assemblies to the hand-held fluid tester 10 shown in the preferred embodiments or these additional probes may be used in substitution for the first and second electrodes 42 and 44 shown for fluid tester 10.

The new and improved portable, hand-held fluid tester in accordance with the present invention provides for repeatable testing by providing a constant test volume of fluid being tested by virtue of the fixed fluid reservoir and spillway arrangement molded into tester body housing 12. The electrical connection and assembly of the probes to the circuit board is made more reliable by making direct circuit board mounting of the probes rather than providing a leaded connection between probes and circuit board. A unique temperature probe is provided which places a thermistor within a thermal well of a metal cylinder which provides for better heat transfer than conventionally used potting compounds. Each of the probes and electrodes are separately mounted and sealably inserted into the tester body and can easily be replaced or repaired in use and reassembled with the testing circuit on the printed circuit board with relative ease.

What is claimed is:

1. A portable, hand-held fluid tester comprising:
a tester body configured to be held in a hand including an upper surface and an opposed bottom surface, a first recess extending inwardly from the upper surface to a first end wall defining a fluid reservoir, a second recess extending inwardly from the upper surface to a second end wall defining an overflow reservoir disposed adjacent to the fluid reservoir, a spillway surface extending between and interconnecting the fluid reservoir to the overflow reservoir, a third recess extending inwardly from the bottom surface to a third end wall defining a test circuit receiving recess; at least one test probe member extending from the third end wall into the first end wall and fluid reservoir and sealingly engaged in the tester body, a test circuit in the test circuit receiving recess operably connected with said at least one probe member for measuring at least one parameter of a test fluid introduced in the fluid reservoir and reporting a result for the at least one parameter measurement; and
a cover member releasably secured to the tester body closing off an opening of the third recess.

2. A portable, hand-held tester as defined in claim 1, wherein the angled spillway surface is configured to overflow excess test fluid introduced in the fluid reservoir from the fluid reservoir to the overflow reservoir thereby defining a maximum fluid volume for the fluid reservoir.

3. A portable, hand-held tester as defined in claim 1, wherein the test circuit comprises a printed circuit substrate mounted in the test circuit receiving recess.

4. A portable, hand-held tester as defined in claim 1, wherein said at least one test probe member comprises a pair of cylindrical metallic electrodes each having a front end and an opposed rear end, said electrodes being mounted in the tester body so that the electrodes extend into the third end wall with the front end of each electrode flush mounted in said first end wall, each electrode including an external o-ring groove and o-ring and being sealingly mounting the electrode in the tester body.

5. A portable, hand-held fluid tester as defined in claim 4, wherein the rear end of each electrode includes a threaded recess, the test circuit comprises a printed circuit substrate mounted in the test receiving cavity and a pair of threaded mounting screws extend through the printed circuit substrate and each is threadingly engaged in a threaded recess of an electrode thereby electrically and mechanically connecting the electrodes with the test circuit.

6. A portable, hand-held fluid tester as defined in claim 1, further comprising an input keypad disposed on the upper surface of the tester body in electrical communication with the test circuit.

7. A portable, hand-held fluid tester as defined in claim 1, further comprising a display window in the upper surface of the tester body and said test circuit comprising an LCD or LED display mounted so that the LCD or LED display shows through the display window.

8. A portable, hand-held fluid tester as defined in claim 1, further comprising a temperature probe including a hollow cylindrical metallic housing having a closed front end and an opposed open rear end with an elongate cylindrical thermistor receiving recess defined therein, a thermally conductive grease disposed in the thermistor receiving recess adjacent the closed front end and a thermistor operably connected with the test circuit disposed in the thermistor receiving recess adjacent the closed front end in contact with the thermally conductive grease, said temperature probe extending into the third end wall with its closed front end extending into the first end wall and fluid reservoir and being sealingly mounted in the tester housing.

9. A portable, hand-held tester as defined in claim 8, wherein said temperature probe includes an external o-ring groove on the cylindrical metallic housing and an o-ring disposed in the o-ring groove compressingly sealingly engaged with the tester housing.

10. A portable, hand-held tester as defined in claim 1, wherein said tester body comprises a moldable thermoplastic polymer material.

11. A portable, hand-held tester as defined in claim 1, wherein said tester body comprises a unitary thermoplastic polymer molding.

12. A portable, hand-held tester as defined in claim 1, wherein said at least one test probe member in combination with said test circuit is adapted to measure a parameter of a test fluid introduced in the fluid reservoir selected from the group consisting of: electrical conductivity, pH, turbidity and oxidation-reduction potential (ORP).

13. A portable hand-held fluid tester as defined in claim 1, wherein said second recess is deeper than said first recess.

14. A portable, hand-held tester as defined in claim 1, wherein the spillway surface is angled and interconnects an upper end of the fluid reservoir to an upper end of the overflow reservoir.

15. A hand-held fluid tester comprising:
a tester body having a top, outer surface;
a fluid test reservoir defined in the tester body, the fluid test reservoir having an upper fill opening at the top, outer surface of the tester body and extending downward into the tester body;
an overflow reservoir defined in the tester body;
an overflow spillway fluidly connected to the fluid test reservoir and the overflow reservoir;
at least one test probe extending into the fluid test reservoir; and
an electrical test circuit connected to the at least one test probe.

16. A method of testing fluid in a hand-held fluid tester comprising the steps of:
introducing fluid into a fluid test reservoir defined in the fluid tester through an opening in an outer top surface of the fluid tester in which the test reservoir extends downward from the opening;
filling the test reservoir with the fluid to a desired level;
flowing excess fluid from the fluid test reservoir to an overflow reservoir defined in the fluid tester; and
testing the fluid in the fluid test reservoir with at least one test probe connected to an electrical test circuit.

\* \* \* \* \*